United States Patent
Hsieh et al.

(10) Patent No.: US 7,734,079 B2
(45) Date of Patent: Jun. 8, 2010

(54) METHODS AND APPARATUS FOR IMAGE RECONSTRUCTION

(75) Inventors: Jiang Hsieh, Brookfield, WI (US); Fang Frank Dong, New Berlin, WI (US); Thomas John Myers, Wauwatosa, WI (US); George Seidenschnur, Waukesha, WI (US); Anne Marie Conry, Wauwatosa, WI (US); Zachary William Sopcak, Milwaukee, WI (US); Brian Grekowicz, Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 423 days.

(21) Appl. No.: 11/158,611

(22) Filed: Jun. 22, 2005

(65) Prior Publication Data

US 2006/0078185 A1    Apr. 13, 2006

Related U.S. Application Data

(60) Provisional application No. 60/613,997, filed on Sep. 28, 2004.

(51) Int. Cl.
*G06K 9/00*     (2006.01)

(52) U.S. Cl. .................. 382/131; 382/199; 382/284; 359/559; 713/186; 378/15; 378/8

(58) Field of Classification Search .............. 382/131
See application file for complete search history.

(56) References Cited

U.S. PATENT DOCUMENTS

| 5,151,822 | A | * | 9/1992 | Hekker et al. | 359/559 |
| 5,663,995 | A | | 9/1997 | Hu | |
| 5,680,460 | A | * | 10/1997 | Tomko et al. | 713/186 |
| 5,692,072 | A | * | 11/1997 | Hashimoto | 382/199 |
| 5,712,912 | A | * | 1/1998 | Tomko et al. | 713/186 |
| 5,732,118 | A | | 3/1998 | Hsieh | |
| 5,974,109 | A | | 10/1999 | Hsieh | |
| 6,028,909 | A | * | 2/2000 | Zmora | 378/15 |
| 6,061,423 | A | * | 5/2000 | Hsieh | 378/15 |
| 6,173,029 | B1 | | 1/2001 | Xie et al. | |
| 6,185,271 | B1 | | 2/2001 | Kinsinger | |
| 6,215,841 | B1 | * | 4/2001 | Hsieh | 378/8 |
| 6,243,437 | B1 | * | 6/2001 | Hu et al. | 378/8 |
| 6,421,411 | B1 | | 7/2002 | Hsieh | |
| 6,466,640 | B1 | | 10/2002 | Taguchi | |
| 6,490,333 | B1 | | 12/2002 | Hsieh | |
| 6,597,756 | B1 | | 7/2003 | Basu et al. | |
| 6,647,084 | B1 | | 11/2003 | Hsieh | |
| 6,961,478 | B2 | * | 11/2005 | Inoue | 382/284 |
| 2002/0012477 | A1 | * | 1/2002 | Inoue | 382/284 |

OTHER PUBLICATIONS

US 6,055,290, 04/2000, Xie et al. (withdrawn)

* cited by examiner

*Primary Examiner*—Samir A Ahmed
*Assistant Examiner*—Tsung-Yin Tsai
(74) *Attorney, Agent, or Firm*—Dean Small; Small Patent Law Group

(57) ABSTRACT

Methods and apparatus for producing an image of an object with a multi-slice imaging apparatus having a row of detectors are provided. The method includes generating a first partial image using projection data acquired at a first imaging position in a step-and-shoot imaging mode, generating a second partial image using projection data acquired at a second imaging position, and combining the partial images to form a final image.

26 Claims, 3 Drawing Sheets

METHODS AND APPARATUS FOR IMAGE RECONSTRUCTION

CROSS REFERENCE TO RELATED APPLICATIONS

This application claims priority to U.S. provisional patent application with Ser. No. 60/613,997, filed on Sep. 28, 2004, and hereby incorporated by referenced in its entirety.

BACKGROUND OF THE INVENTION

This invention relates generally to the reconstruction of images and more particularly to methods and apparatus for reconstruction of step-and-shoot CT images using partial image data from adjacent scan positions.

Typical multi-slice CT protocols utilize a helical mode for head scans. The advantages of the helical scans are the ability to reconstruct images at arbitrary locations and the elimination of inter-scan delays. The disadvantage of the helical mode, on the other hand, is the production of image artifacts. When the patient table moves during data acquisition, projection interpolation may be performed to estimate projection samples at the reconstruction location. The interpolation process assumes that the patient table location is known for every projection view. In practice, however, due to technical limitations the patient table location may not be known accurately. As a result, certain assumptions may be made relative to the table motion. For example, an assumption that the table moves at a constant speed and the table locations can be directly calculated from its speed and time may be made. However image artifacts may be generated if the table does not index at a constant speed.

BRIEF DESCRIPTION OF THE INVENTION

In one embodiment, a method for producing an image of an object with a multi-slice imaging apparatus having a row of detectors are provided. The method includes generating a first partial image using projection data acquired at a first imaging position in a step-and-shoot imaging mode, generating a second partial image using projection data acquired at a second imaging position, and combining the partial images to form a final image.

In another embodiment, a computed tomographic (CT) imaging system for reconstructing an image of an object is provided. The imaging system includes a detector array, at least one radiation source, and a computer coupled to said detector array and said radiation source, said computer configured to generate a first partial image using projection data acquired at a first imaging position in a step-and-shoot imaging mode, generate a second partial image using projection data acquired at a second imaging position, and combine the partial images to form a final image.

In yet another embodiment, a computer readable medium encoded with a program code segment executable by a computer for reconstructing an image of an object is provided. The program code segment is programmed to instruct the computer to generate a first partial image using projection data acquired at a first imaging position in a step-and-shoot imaging mode, generate a second partial image using projection data acquired at a second imaging position, and combine the partial images to form a final image.

DETAILED DESCRIPTION OF THE INVENTION

Figure 1:
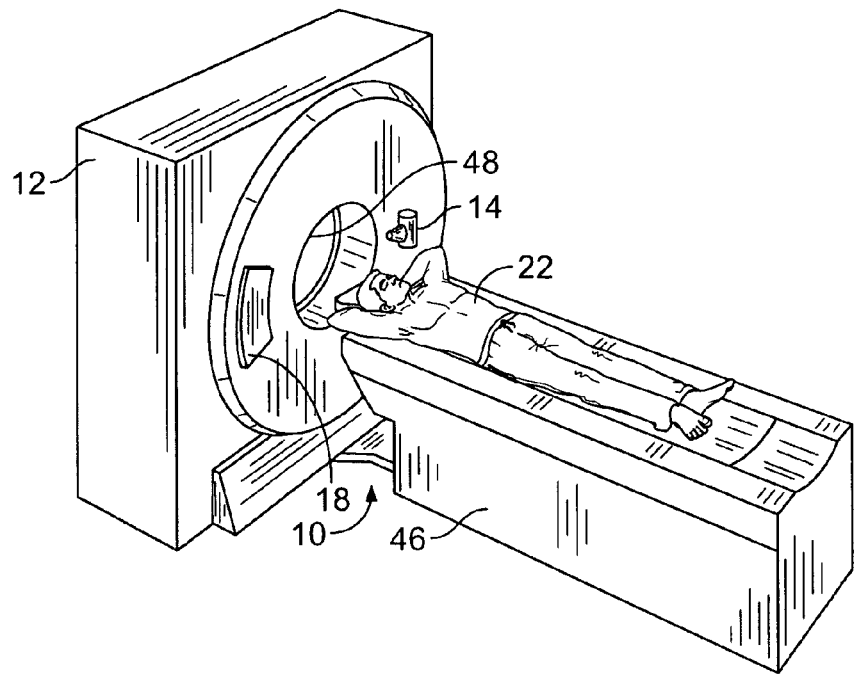
FIG. 1 is a perspective view of a configuration of a computed tomographic imaging apparatus.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the acquired data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image. Thus, methods and apparatus are described herein that have a technical effect of producing a three-dimensional (3D) image of a scanned object.

Figure 2:
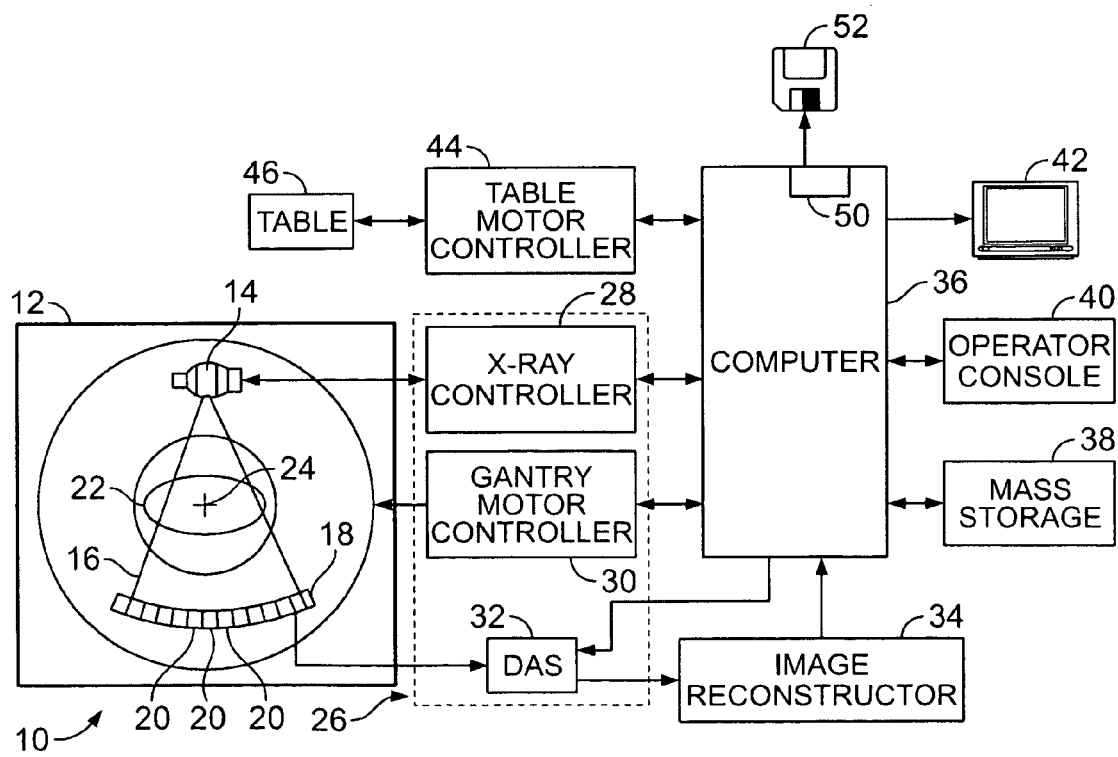
FIG. 2 is a functional block diagram of the computed tomographic imaging apparatus illustrated in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has a radiation source such as an x-ray tube 14 (also called x-ray source 14 herein) that projects a beam of radiation such as x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging radiation (e.g., x-ray) beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 or other suitable display device allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). In some configurations, computer 36 and/or image reconstructor 34 is/are programmed to perform functions described herein. Also, as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Figure 3:
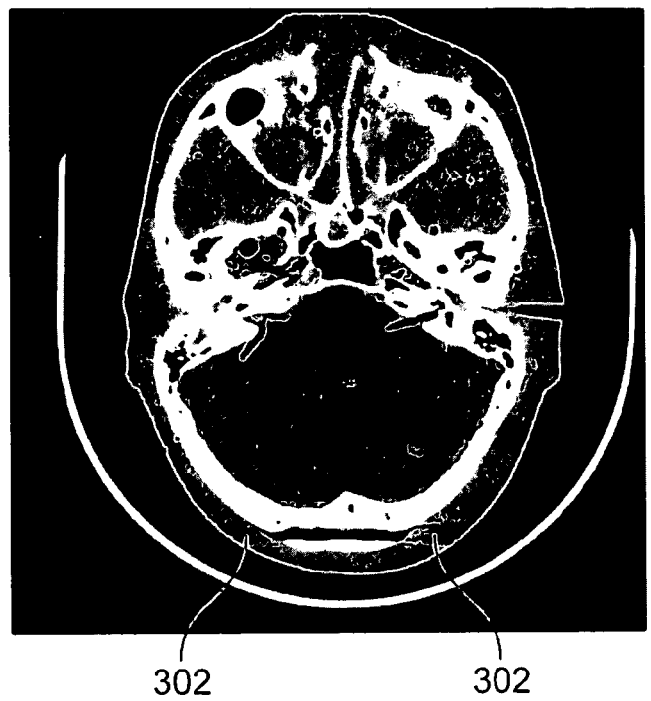
FIG. 3 is an illustration of an exemplary human skull phantom image acquired at a gantry rotation speed of 0.5 s.
Figure 4:
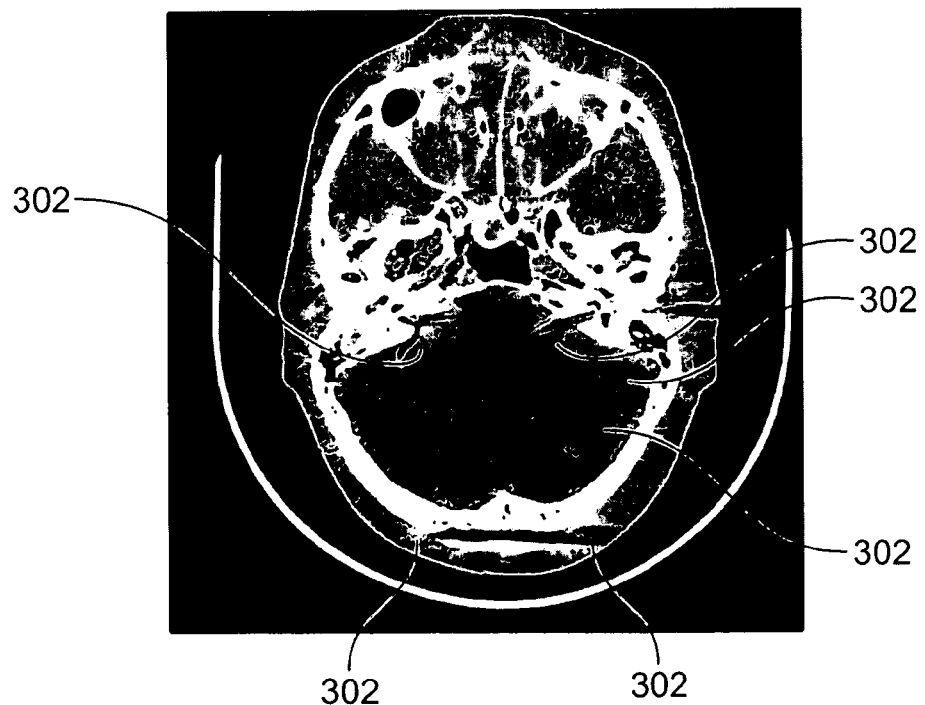
FIG. 4 is an illustration of an exemplary human skull phantom image acquired at a gantry rotation speed of 0.8 s.

FIGS. 3 and 4 illustrate a human skull phantom image 300 and 400 respectively, acquired at two different gantry rotation speeds using a helical scan protocol. FIG. 3 shows a human skull phantom image acquired at a gantry rotation speed of 0.5 s and FIG. 4 shows a human skull phantom image acquired at a gantry rotation speed of 0.8 s. The two scans were acquired at the same helical pitch (15/16), the table speeds for the two scans were different (18.75 mm/s and 11.72 mm/s, respectively). Table jitter may vary substantially depending on different speed ranges used during a scan. The jitter magnitude may be magnified or reduced due to the resonant frequencies of the patient table and of the system mechanical components. A CT system may provide multiple gantry rotational speeds and helical pitches to optimize clinical performance. For example, on a 16-slice scanner, there may be four different helical pitches and six different gantry speeds. The combination of pitches and gantry speeds corresponds to twenty four different table indexing speeds. As such a patient table may have a plurality of resonant frequencies, at least some of which may affect helical scanning imaging of the patient. Table jitter may result in artifacts 302 in the scan image that are not related to structures in the object being scanned. Artifacts 302 may appear as smeared areas of the image that are not related to actual structures in the object being scanned, but rather are unintended products of the reconstruction of the image.

Figure 5:
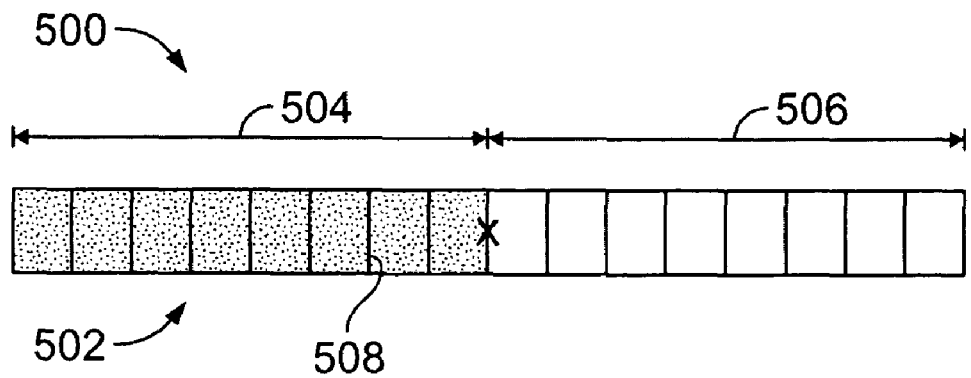
FIG. 5 is an illustration of two exemplary step-and-shoot data acquisitions for an 8-slice CT scanner.

FIG. 5 illustrates two exemplary step-and-shoot data acquisitions 500 for an 8-slice CT scanner. When CT scans are acquired in a step-and-shoot mode, the undesirable characteristics of the table motion may be eliminated, because in a step-and-shoot mode, the table remains stationary during the entire data acquisition. Because each reconstructed image corresponds to projection data acquired on a particular row, overlapped images may not be available. Overlapped reconstruction is used to avoid under-sampling artifacts in reformatted or 3D images. A row of detector elements 502 is shown in a first axial scan position 504 and a second axial scan position 506. As shown there is no overlap between the first and second axial scan positions. A location "X" represents a location where an estimation of a projection is desired.

In cone beam reconstruction, images can be generated in any of a plurality of arbitrary axial locations, such as between adjacent detector elements, by interpolating during the backprojection process. A similar process is also applicable to the 2D backprojection process. When the cone beam angle is small, such as with a fan beam, the image artifact due to cone beam may be ignored. For example, the cone angle may be only 0.5° for data acquired with a 16×0.625 mm configuration.

An image may be generated between the locations of two detector row locations, for example, at a location 508, by interpolating a set of projections at the corresponding locations using:

$$p(\gamma, \beta, z) = \sum_{k=-K}^{K} w(k) p(\gamma, \beta, k + i_z), \text{ where} \quad (1)$$

z specifies the location of the reconstructed image in terms of detector rows;

$i_z$ is the integer portion of z, w(k) is the interpolation coefficients, and p(γ, γ, i) represents a projection sample acquired with detector angle γ, projection angle β, and detector row i.

A set of projections may be interpolated at locations between detector rows 1 and 8 for a 8-slice CT scanner. However, when estimating a projection outside the boundary of detector rows, formula (1) may no longer produce satisfactory results because estimating the data outside the sampling range uses extrapolation rather than interpolation. In some known instances, extrapolation is less reliable and produces higher noise level and artifacts. Projections at adjacent acquisition locations are used to permit use of interpolation during a step and shoot scan, for example, first axial scan position 504 and second axial scan position 506 of a two step-and-shoot data acquisition for an 8-slice CT scanner. In the exemplary embodiment, for an estimation of the projection at location "X", projections from first axial scan position 504 and second axial scan position 506 may be used.

In operation, projection angle misalignment may introduce errors even in a step and shoot mode. For example, in the step-and-shoot data acquisition mode, the scanner x-ray tube may be turned off after the data acquisition for first axial scan position 504 is completed. The table is indexed to second axial scan position 506 and the x-ray tube is turned on for the next acquisition. When the x-ray tube is turned on, it is unlikely that the tube will be in the exact angular position as the previous acquisition. Typically, the view angular offset is a fraction rather than an integer view index.

To generate images outside the detector row 502, a first image using the projection of first axial scan position 504 is generated and second image using the projection of second axial scan position 506 is generated. The projection acquired at first axial scan position 504 is weighted and a first partial image, $f_1(x, y, z)$, is reconstructed using:

$$p_1(\gamma, \beta, z) = \sum_{k=-K}^{0} w(k) p(\gamma, \beta, k + i_z) \quad (2)$$

The projection acquired at second axial scan position 506 is weighted and a second partial image, $f_2(x, y, z)$, is reconstructed using:

$$p_2(\gamma, \beta, z) = \sum_{k=1}^{K} w(k) p(\gamma, \beta, k + i_z) \quad (3)$$

The final image is obtained by combining the two partial images:

$$f(x,y,z) = f_1(x,y,z) + f_2(x,y,z) \quad (4)$$

Alternatively, because the filtered backprojection process is linear, the interpolation in projection space can be performed directly on the reconstructed images. That is, if we denote by f(x, y, i) the reconstructed image at location i, the resulting image, f(x, y, z), is:

$$f(x, y, z) = \sum_{k=-K}^{K} w(k) f(x, y, k + i_z) \quad (5)$$

Figure 6:
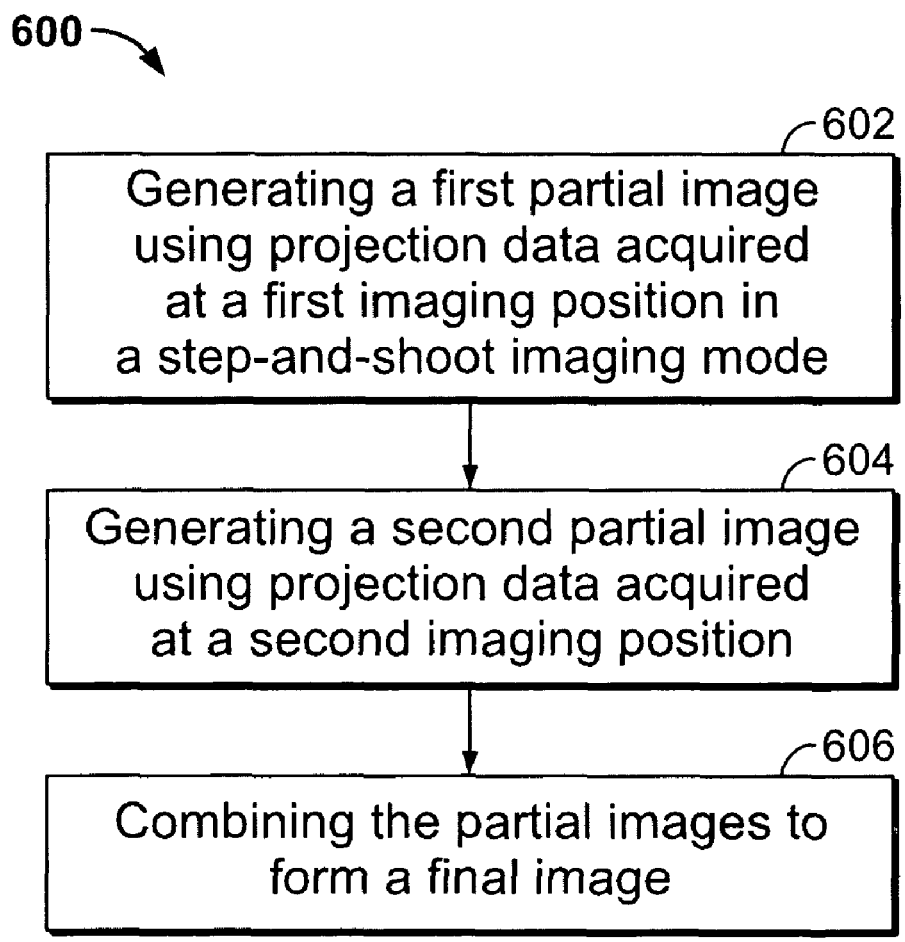
FIG. 6 is a flow chart of an exemplary method of reconstructing an image using projection data from outside a detector row of elements.

FIG. 6 is an exemplary method 600 for reconstructing an image of an object with a multi-slice imaging apparatus having a row of detectors using a step and shoot scanning mode. Method 600 includes generating 602 a first partial image using projection data acquired at a first imaging position in a step-and-shoot imaging mode. The first imaging position may correspond to an axial position of a patient table that is configured to move a patient axially to each imaging position of a scan. A second partial image is generated 604 using projection data acquired at a second imaging position. In the exemplary embodiment, the second imaging position is axially adjacent to the first imaging position and does not overlap the first imaging position. The two partial images are combined 606 to form a final image.

In the exemplary embodiment, the partial images are weighted to account for an axial distance between the respective detector and an axial location of the final image.

A technical effect of the above described methods enable substantial elimination of artifacts in scan images due to table jitter during a helical scan using a step and shoot mode of acquisition. Specifically, a method of interpolation of projections from end of detector row elements permits substantial elimination artifacts during a step and shoot mode of data acquisition.

The above-described embodiments of methods and apparatus for image reconstruction during a step and shoot scan are cost-effective and highly reliable for facilitating image reconstruction when projection overlap is unavailable, for example during an axial step and shoot mode of image data acquisition.

While the invention has been described in terms of various specific embodiments, those skilled in the art will recognize that the invention can be practiced with modification within the spirit and scope of the claims.

What is claimed is:

1. A method for producing an image of an object with a multi-slice imaging apparatus, said method comprising:
   generating a first partial image using projection data acquired at a first imaging position in a step-and-shoot imaging mode, wherein the first projection data is weighted using:

$$p_2(\gamma, \beta, z) = \sum_{k=1}^{K} w(k) p(\gamma, \beta, k + i_z)$$

z specifies the location of the reconstructed image in terms of detector rows,
   $i_z$ is the integer portion of z,
   w(k) is the interpolation coefficients, and
   p(γ, β, i) represents a projection sample acquired with detector angle γ, projection angle β, and detector row i
   generating a second partial image using projection data acquired at a second single imaging position; and
   combining the partial images to form a final image.

2. The method in accordance with claim 1 wherein the first and the second imaging positions are axially adjacent.

3. The method in accordance with claim 1 wherein combining the partial images comprises combining the partial images that have been weighted to account for an axial distance between the detector and an axial location of the final image.

4. The method in accordance with claim 1 further comprising generating an image between detector row locations by interpolating a set of projections acquired at the corresponding locations.

5. The method in accordance with claim 4 further comprising interpolating a set of projections acquired at the corresponding locations using:

$$p(\gamma, \beta, z) = \sum_{k=-K}^{K} w(k) p(\gamma, \beta, k + i_z), \text{ where}$$

z specifies the location of the reconstructed image in terms of detector rows,
   $i_z$ is the integer portion of z,
   w(k) is the interpolation coefficients, and
   p(γ, β, i) represents a projection sample acquired with detector angle γ, projection angle β, and detector row i.

6. The method in accordance with claim 1 further comprising interpolating between the images to form a final image using:

$$f(x, y, z) = \sum_{k=-K}^{K} w(k) f(x, y, k + i_z), \text{ where}$$

f(x, y, i) is the reconstructed image at location i, and
   the final image is, f(x, y, z).

7. A method in accordance with claim 1 wherein the second partial image is consecutive and non-overlapping with the first partial image.

8. A method in accordance with claim 1 further comprising interpolating projection data for an area outside a boundary of the partial images to form the final image.

9. A method for producing an image of an object with a multi-slice imaging apparatus, said method comprising:
   generating a first partial image using projection data acquired at a first single imaging position in a step-and-shoot imaging mode;
   generating a second partial image using projection data acquired at a second single imaging position, wherein the second projection data is weighted using:

$$p_2(\gamma, \beta, z) = \sum_{k=1}^{K} w(k) p(\gamma, \beta, k + i_z)$$

z specifies the location of the reconstructed image in terms of detector rows,
   $i_z$ is the integer portion of z,
   w(k) is the interpolation coefficients, and
   p(γ, γ, i) represents a projection sample acquired with detector angle γ, projection angle β, and detector row i
   combining the partial images to form a final image.

10. A computed tomographic (CT) imaging system for reconstructing an image of an object, said imaging system comprising:
    a detector array;
    at least one radiation source; and
    a computer coupled to said detector array and said radiation source, said computer configured to:
    generate a first partial image using projection data acquired at a first imaging position in a step-and-shoot imaging mode, wherein the first projection data partial image is weighted using:

$$p_2(\gamma, \beta, z) = \sum_{k=1}^{K} w(k) p(\gamma, \beta, k + i_z)$$

z specifies the location of the reconstructed image in terms of detector rows,
    $i_z$ is the integer portion of z,
    w(k) is the interpolation coefficients, and
    p(γ, β, i) represents a projection sample acquired with detector angle γ, projection angle β, and detector row i
    generate a second partial image using projection data acquired at a second imaging position; and
    combine the partial images to form a final image.

11. The computed tomographic (CT) imaging system in accordance with claim 10 wherein said computer is further configured to weight the partial images to account for an axial distance between the detector and an axial location of the final image.

12. The computed tomographic (CT) imaging system in accordance with claim 10 wherein the first and the second axial imaging positions are axially adjacent.

13. The computed tomographic (CT) imaging system in accordance with claim 10 wherein the second partial image is weighted using:

$$p_2(\gamma, \beta, z) = \sum_{k=1}^{K} w(k) p(\gamma, \beta, k + i_z)$$

z specifies the location of the reconstructed image in terms of detector rows, $i_z$ is the integer portion of z, w(k) is the interpolation coefficients, and p(γ, β, i) represents a projection sample acquired with detector angle γ, projection angle β, and detector row i.

14. The computed tomographic (CT) imaging system in accordance with claim 10 wherein said computer is further configured to generate an image between detector row locations by interpolating a set of projections acquired at the corresponding locations.

15. The computed tomographic (CT) imaging system in accordance with claim 14 wherein said computer is further configured to interpolate a set of projections acquired at the corresponding locations using:

$$p(\gamma, \beta, z) = \sum_{k=-K}^{K} w(k)p(\gamma, \beta, k + i_z), \text{ where}$$

z specifies the location of the reconstructed image in terms of detector rows, $i_z$ is the integer portion of z, w(k) is the interpolation coefficients, and p(γ, β, i) represents a projection sample acquired with detector angle γ, projection angle β, and detector row i.

16. The computed tomographic (CT) imaging system in accordance with claim 10 wherein said computer is further configured to interpolate between the images using:

$$f(x, y, z) = \sum_{k=-K}^{K} w(k)f(x, y, k + i_z), \text{ where}$$

f(x, y, i) is the reconstructed image at location i, and the final image is, f(x, y, z).

17. A CT imaging system in accordance with claim 10 wherein said computer is further configured to:

backproject the adjacent axial scans; and filter the backprojected scans.

18. A computer readable medium encoded with a program code segment executable by a computer for reconstructing an image of an object, said segment programmed to instruct the computer to:

generate a first partial image using projection data acquired at a first imaging position in a step-and-shoot imaging mode wherein the first partial image is weighted using:

$$p_2(\gamma, \beta, z) = \sum_{k=1}^{K} w(k)p(\gamma, \beta, k + i_z)$$

z specifies the location of the reconstructed image in terms of detector rows, $i_z$ is the integer portion of z, w(k) is the interpolation coefficients, and p(γ, β, i) represents a projection sample acquired with detector angle γ, projection angle β, and detector row i generate a second partial image using protection data acquired at a second imaging position: and combine the partial images to form a final image.

19. The computer readable medium in accordance with claim 18 wherein the first and the second imaging positions are axially adjacent.

20. The computer readable medium in accordance with claim 18 wherein said program code segment is further programmed to combine the partial images that have been weighted to account for an axial distance between the detector and an axial location of the final image.

21. The computer readable medium in accordance with claim 18 wherein the second partial image is weighted using:

$$p_2(\gamma, \beta, z) = \sum_{k=1}^{K} w(k)p(\gamma, \beta, k + i_z)$$

z specifies the location of the reconstructed image in terms of detector rows, $i_z$ is the integer portion of z, w(k) is the interpolation coefficients, and p(γ, β, i) represents a projection sample acquired with detector angle γ, projection angle β, and detector row i.

22. The computer readable medium in accordance with claim 18 wherein said program code segment is further programmed to generate an image between detector row locations by interpolating a set of projections acquired at the corresponding locations.

23. The computer readable medium in accordance with claim 18 wherein said program code segment is further programmed to interpolate a set of projections acquired at the corresponding locations using:

$$p(\gamma, \beta, z) = \sum_{k=-K}^{K} w(k)p(\gamma, \beta, k + i_z), \text{ where}$$

z specifies the location of the reconstructed image in terms of detector rows, $i_z$ is the integer portion of z, w(k) is the interpolation coefficients, and p(γ, β, i) represents a projection sample acquired with detector angle γ, projection angle β, and detector row i.

24. The computer readable medium in accordance with claim 18 wherein said program code segment is further programmed to interpolate between the images using:

$$f(x, y, z) = \sum_{k=-K}^{K} w(k)f(x, y, k + i_z), \text{ where}$$

f(x, y, i) is the reconstructed image at location i, and the final image is, f(x, y, z).

25. The computer readable medium in accordance with claim 18 wherein the second partial image is consecutive and non-overlapping with the first partial image.

26. The computer readable medium in accordance with claim 18 wherein said program code segment is further programmed to interpolate projection data for an area outside a boundary of the partial images to form the final image.

* * * * *